(12) United States Patent
Cappelleri et al.

(10) Patent No.: US 10,806,489 B2
(45) Date of Patent: Oct. 20, 2020

(54) SYSTEMS AND METHODS FOR PERFORMING A SURGICAL PROCEDURE

(71) Applicant: Purdue Research Foundation, West Lafayette, IN (US)

(72) Inventors: David John Cappelleri, West Lafayette, IN (US); Benjamin Varughese Johnson, West Lafayette, IN (US); Brian Anthony Cole, Montclair, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 23 days.

(21) Appl. No.: 15/871,622

(22) Filed: Jan. 15, 2018

(65) Prior Publication Data

US 2018/0132891 A1 May 17, 2018

Related U.S. Application Data

(63) Continuation-in-part of application No. 15/222,998, filed on Jul. 29, 2016, now Pat. No. 10,709,324.
(Continued)

(51) Int. Cl.
*A61B 17/34* (2006.01)
*A61B 17/00* (2006.01)
(Continued)

(52) U.S. Cl.
CPC .......... *A61B 17/3421* (2013.01); *A61B 1/005* (2013.01); *A61B 1/0055* (2013.01);
(Continued)

(58) Field of Classification Search
CPC ............ A61B 1/00087; A61B 1/00098; A61B 1/00131; A61B 1/00133; A61B 1/00135;
(Continued)

(56) References Cited

U.S. PATENT DOCUMENTS 5,431,645 A * 7/1995 Smith ................ A61B 18/1445
606/1
7,524,284 B2 * 4/2009 Murakami ......... A61B 1/00059
600/104
(Continued)

FOREIGN PATENT DOCUMENTS

JP          09000492 A  *  1/1997   ......... A61B 1/00133
WO    WO-2014125498 A2 *  8/2014   ....... A61B 17/00234

*Primary Examiner* — Ryan N Henderson
(74) *Attorney, Agent, or Firm* — Hartman Global IP Law; Gary M. Hartman; Domenica N. S. Hartman

(57) ABSTRACT

Systems and methods for performing surgical procedures. Such a system includes a cannula having a tubular body and a distal end is sized and configured to be inserted into a body cavity. The system further includes a tool passing through a first port at s proximal end of the cannula, extending through the cannula, and protruding from the distal end of the cannula through a second port. The tool has a working element on a distal end of a shaft thereof. The working element is capable of articulation relative to the shaft and rotation relative to the cannula, and the tool is adapted for translation and rotation relative to the cannula. The system further includes a control system and actuator that articulate the tip of the working element relative to the shaft of the tool.

17 Claims, 13 Drawing Sheets

Related U.S. Application Data

(60) Provisional application No. 62/199,733, filed on Jul. 31, 2015.

(51) Int. Cl.
  *A61B 17/28* (2006.01)
  *A61B 17/29* (2006.01)
  *A61B 1/00* (2006.01)
  *A61B 1/005* (2006.01)
  *A61B 34/30* (2016.01)
  *A61B 90/30* (2016.01)

(52) U.S. Cl.
  CPC .... *A61B 1/00154* (2013.01); *A61B 17/00234* (2013.01); *A61B 17/28* (2013.01); *A61B 17/29* (2013.01); *A61B 17/3423* (2013.01); *A61B 34/30* (2016.02); *A61B 90/30* (2016.02); *A61B 2017/00305* (2013.01); *A61B 2017/00323* (2013.01); *A61B 2017/294* (2013.01); *A61B 2017/2905* (2013.01); *A61B 2017/2906* (2013.01); *A61B 2017/2908* (2013.01); *A61B 2017/2927* (2013.01); *A61B 2017/3445* (2013.01); *A61B 2034/301* (2016.02)

(58) Field of Classification Search
  CPC ............ A61B 1/00147; A61B 1/00154; A61B 1/0016; A61B 1/01; A61B 2017/3455; A61B 2017/00305; A61B 2017/00323; A61B 2017/294; A61B 2017/2905; A61B 2017/2908; A61B 2017/2926; A61B 2017/2927; A61B 34/30; A61B 2034/301; A61B 1/005; A61B 1/0055; A61B 17/3421; A61B 17/3423; A61B 17/00234; A61B 17/28; A61B 17/29
  See application file for complete search history.

(56) References Cited

U.S. PATENT DOCUMENTS

| | | | | |
|---|---|---|---|---|
| 8,414,505 | B1* | 4/2013 | Weitzner | A61B 18/1492 600/585 |
| 2005/0209505 | A1* | 9/2005 | Okada | A61B 1/018 600/106 |
| 2005/0250989 | A1* | 11/2005 | Suzuki | A61B 17/29 600/106 |
| 2005/0267327 | A1* | 12/2005 | Iizuka | A61B 17/219 600/106 |
| 2006/0224162 | A1* | 10/2006 | Suzuki | A61B 17/29 606/106 |
| 2006/0258905 | A1* | 11/2006 | Kaji | A61B 1/00133 600/106 |
| 2007/0100254 | A1* | 5/2007 | Murakami | A61B 1/00133 600/564 |
| 2007/0299305 | A1* | 12/2007 | Murakami | A61B 1/018 600/106 |
| 2008/0103358 | A1* | 5/2008 | Suzuki | A61B 1/00133 600/106 |
| 2008/0200756 | A1* | 8/2008 | Okada | A61B 1/018 600/106 |
| 2008/0262296 | A1* | 10/2008 | Suzuki | A61B 1/00133 600/106 |
| 2008/0294003 | A1* | 11/2008 | Honda | A61B 1/00071 600/114 |
| 2009/0112060 | A1* | 4/2009 | Sugiyama | A61B 1/2736 600/104 |
| 2009/0137872 | A1* | 5/2009 | Bahney | A61B 10/06 600/118 |
| 2010/0022825 | A1* | 1/2010 | Yoshie | A61B 1/00039 600/104 |
| 2015/0250498 | A1* | 9/2015 | Kikuchi | A61B 17/3417 604/67 |
| 2015/0342445 | A1* | 12/2015 | Jones | A61B 1/00133 600/562 |
| 2015/0366572 | A1* | 12/2015 | Sholev | A61B 34/71 606/170 |
| 2016/0030124 | A1* | 2/2016 | Kishi | A61B 1/00149 600/102 |
| 2016/0089181 | A1* | 3/2016 | Johnson | A61B 17/0218 600/424 |
| 2016/0175004 | A1* | 6/2016 | Dejima | A61B 1/00135 600/114 |
| 2016/0296246 | A1* | 10/2016 | Schaller | A61B 17/30 |
| 2016/0310721 | A1* | 10/2016 | Lesser | A61M 5/3216 |
| 2016/0324399 | A1* | 11/2016 | Banju | A61B 1/0016 |
| 2017/0095139 | A1* | 4/2017 | Yanagihara | A61B 17/3415 |
| 2017/0095299 | A1* | 4/2017 | Hendrick | A61B 1/00039 |
| 2017/0245739 | A1* | 8/2017 | Yamamura | A61B 34/30 |
| 2018/0125596 | A1* | 5/2018 | He | A61B 34/71 |

\* cited by examiner

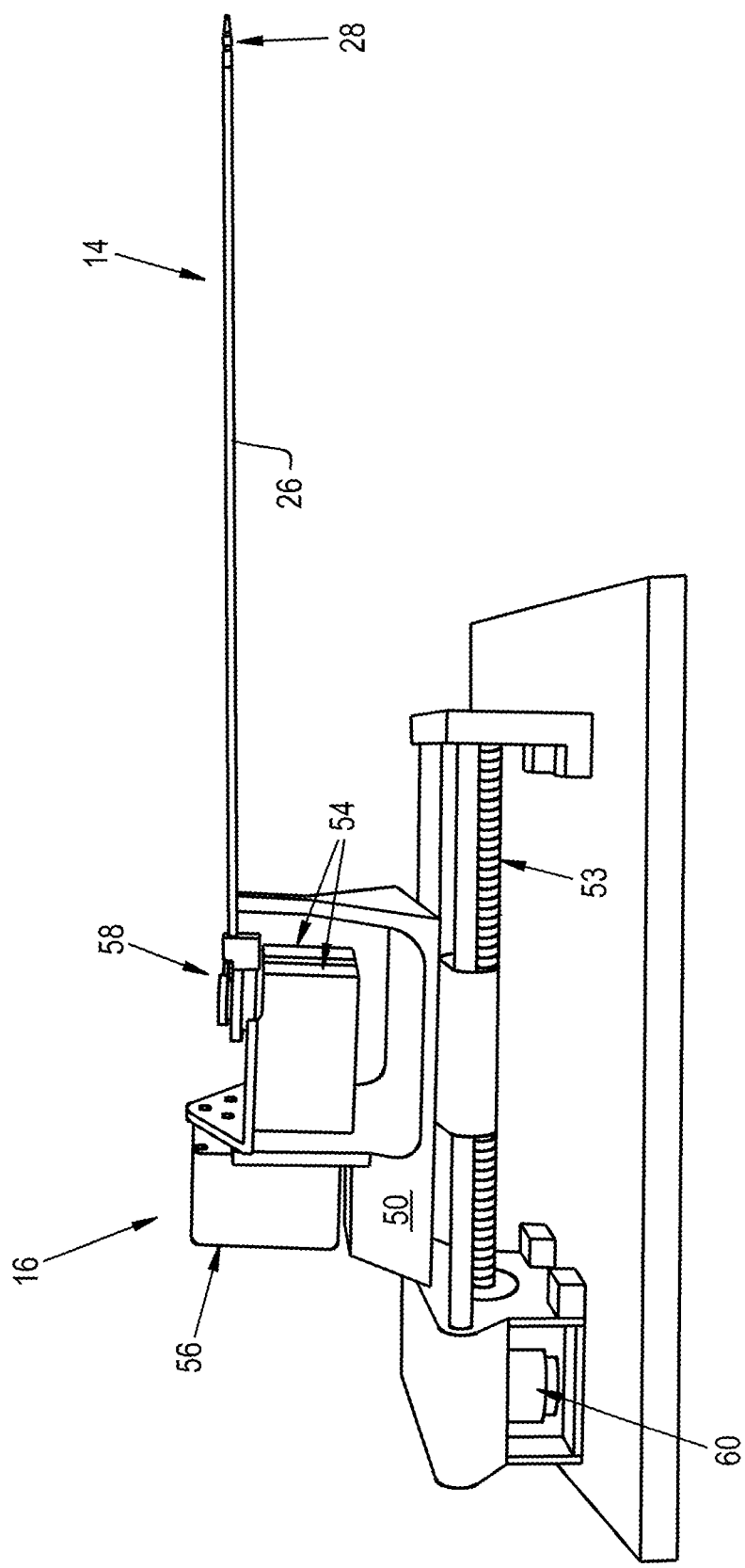

SYSTEMS AND METHODS FOR PERFORMING A SURGICAL PROCEDURE

CROSS REFERENCE TO RELATED APPLICATIONS

This is a continuation-in-part patent application of co-pending U.S. patent application Ser. No. 15/222,998, filed Jul. 29, 2016, which claims the benefit of U.S. Provisional Application No. 62/199,733, filed Jul. 31, 2015. The contents of these prior applications are incorporated herein by reference.

BACKGROUND OF THE INVENTION

The present invention generally relates to tools for working in relatively small working spaces with limited access. The invention particularly relates to instruments for use in minimally invasive surgical procedures.

Pain within an individual's lower back, specifically the lumbar region of the spine, is typically induced by disc herniations or over-compression of the vertebrae. To treat this discomfort, surgeons may perform a microdiscectomy, a minimally invasive (as opposed to open surgery) technique for removing a portion of the herniated disc material that is pressing on the nerve root. While these surgical procedures typically have high success rates and improve patient outcomes relative to more invasive procedures, the tools currently available for performing minimally invasive procedures have limitations.

Surgical instruments commonly available for removing herniated disc material include rigid probes with tips that manipulate and remove tissue. Nonlimiting examples of such instruments include a set of tools available from Richard Wolf Medical Instruments Corporation under the name VERTEBRIS™, a disposable set of tools available from Vertos Medical Inc. under the name Mild®, and a single-use tool available from Stryker Corporation under the name Dekompressor®. Due to the limited working space within the lumbar region of the spine, the limited dexterity of available tools capable of manipulating and removing tissue, and limited vision sometimes encountered during a minimally invasive procedure, a surgeon may become uncomfortable over time and may be forced to operate blindly for portions of the procedure. In addition, movement of a tool, commonly formed of rigid materials to achieve orientations often required during a minimally invasive procedure, can cause inadvertent damage to muscles, soft tissue, and nerve roots.

While most available surgical instruments used in minimally invasive procedures are rigid, some more recent instruments have been disclosed that are based on a flexible backbone structure to provide improved flexibility. However, such tools generally have a relatively large radius of curvature and hence can be used only in relatively large body cavities and similarly sized working spaces. Although surgical tools have been disclosed having diameters less than four millimeters, they are generally expensive to manufacture and require complicated assembly.

Robotic surgical systems are now emerging which are intended to overcome challenges associated with surgical procedures. However, these systems are generally limited in their practical applications due to their size, capabilities, and cost. Additionally, these systems may require extensive sterilization and draping to reduce the risk of infection.

In view of the above, there is an ongoing desire for devices that are capable of use in surgical procedures, for example, minimally invasive procedures such as microdiscectomy, with improved dexterity and vision relative to currently available surgical instruments.

BRIEF DESCRIPTION OF THE INVENTION

The present invention provides systems and methods for performing surgical procedures with improved dexterity and vision relative to systems and methods performed with currently available surgical instruments used in minimally invasive procedures.

According to one aspect of the invention, a system for performing a surgical procedure within a cavity of a living body includes a cannula having a tubular body with at least first and second ports located at proximal and distal ends of the cannula, wherein the distal end is sized and configured to be inserted into the cavity. The system further includes at least a first tool passing through the first port of the cannula, extending through the body of the cannula, and protruding from the distal end of the cannula through the second port. The first tool comprises a shaft and a working element on a distal end of the shaft, wherein at least a portion of the working element is capable of articulation relative to the shaft and rotation relative to the cannula, the working element is configured to perform tasks in the cavity, and the first tool is adapted for translation and rotation relative to the cannula. The system further includes a control system and actuator that articulate the tip of the working element relative to the shaft of the first tool.

Technical effects of a system as described above preferably include the ability to perform tasks of a surgical procedure in a cavity of a living body with improved dexterity and vision relative to currently available surgical instruments used in minimally invasive procedures.

Other aspects and advantages of this invention will be better appreciated from the following detailed description.

BRIEF DESCRIPTION OF THE DRAWINGS

FIG. 8 shows a surgical instrument coupled to an actuator unit in accordance with a nonlimiting embodiment of this invention.

DETAILED DESCRIPTION OF THE INVENTION

Figure 1:
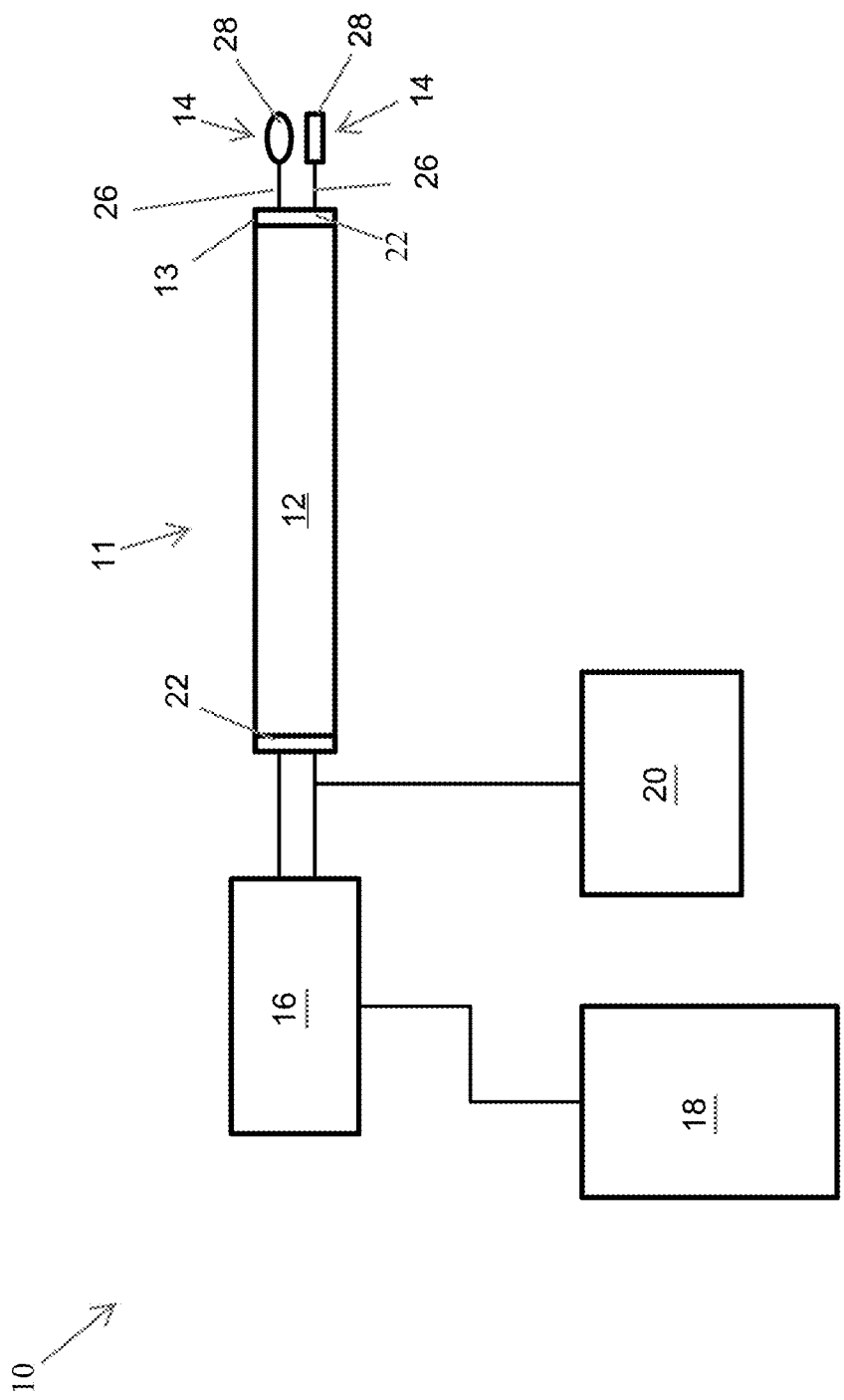
FIG. 1 schematically represents a system comprising a surgical instrument equipped with multiple tools for performing tasks in an enclosed space in accordance with a nonlimiting embodiment of this invention.

FIG. 1 schematically represents a system 10 configured to perform tasks in a confined working space or cavity. Although the system 10 will be described below as being used to perform tasks associated with or required by a minimally invasive surgical procedure within a cavity of a living body, such as but not limited to a microdiscectomy performed in a human being, it is within the scope of the invention that the system 10 could be configured for use in any type of confined working space or cavity. For example, the system 10 may be configured for use in a surgical procedure or other invasive procedures performed on animals, or may be used in a non-medical field to repair or otherwise access and manipulate objects in difficult to access locations. It is within the scope of the invention that the confined working space or cavity in which the system 10 is configured to perform tasks may be relatively small, for example, having a volume of about ten cubic centimeters or less, and as small as about three cubic centimeters or less.

The system 10 includes a surgical instrument 11 functionally coupled to an actuator unit 16. The instrument 11 is represented as comprising a cannula 12 having a distal end 13 sized and configured for insertion through an incision in a patient during a minimally invasive surgical procedure. Although the body of the cannula 12 could have any shape, it is represented in the drawings as having an elongated tubular body. The cannula 12 is configured to allow one or more surgical tools 14 to be routed therethrough, such that a working element 28 of each tool 14 protrudes from the distal end 13 of the cannula 12. The working elements 28 are configured to manipulate and/or remove tissue during the surgical procedure. A control system 18 is provided that enables a surgeon to operate and control the instrument 11, for example, a computer or other processing device with manual controls such a joystick for performing the surgical procedure or on which a computer program is running with software instructions for implementing the surgical procedure. FIG. 1 further represents a monitor 20 for displaying video images captured by a camera within an incision. Such a camera may be incorporated as the working element 28 on one of the tools 14.

Figure 2:
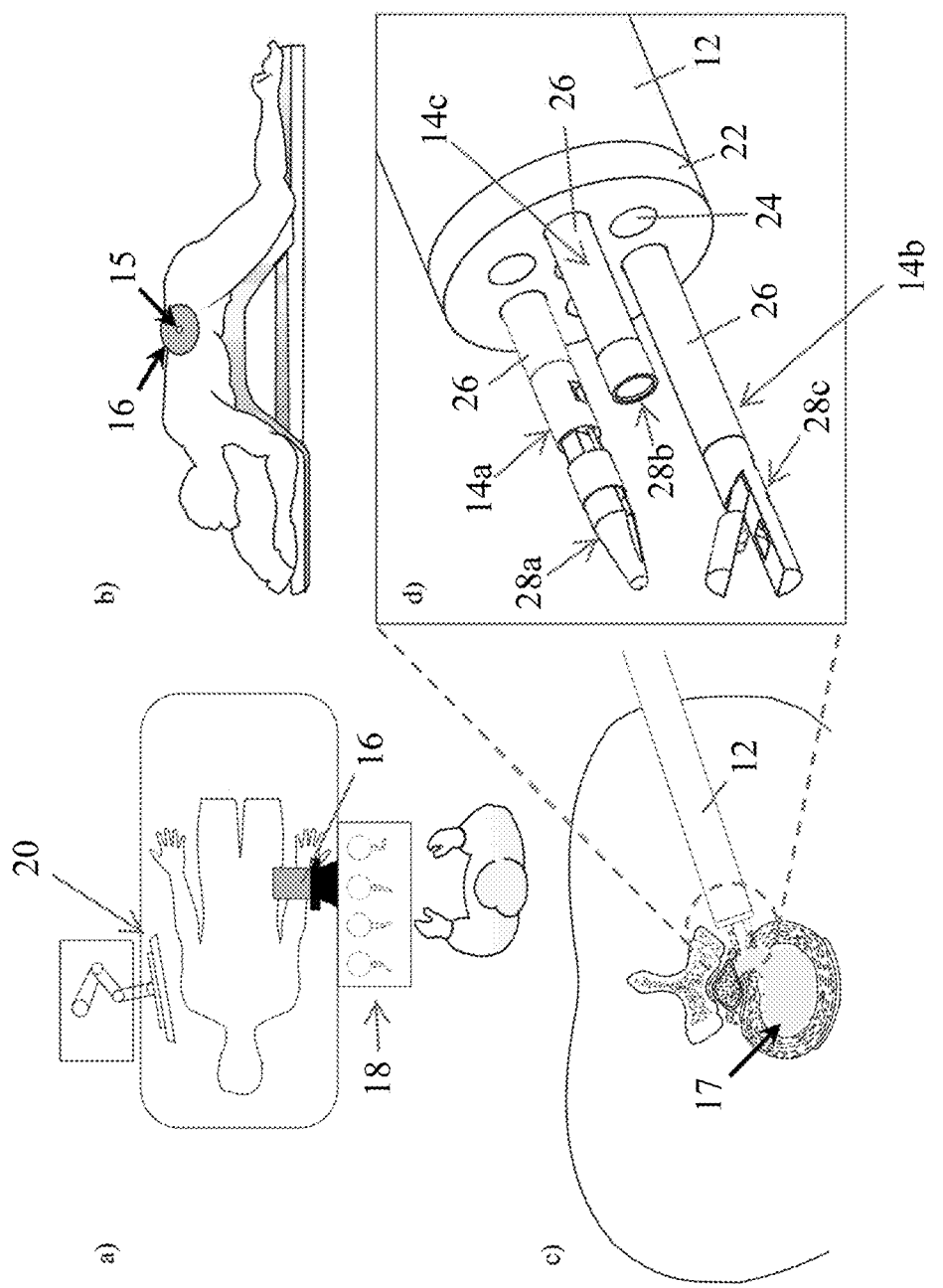
FIG. 2 includes images a, b, c, and d, which schematically represent use of the system of FIG. 1 during a microdiscectomy in accordance with a nonlimiting embodiment of this invention.

Images (a) through (c) of FIG. 2 schematically represent a nonlimiting embodiment of the system 10 as configured for performing a microdiscectomy, during which an incision is made to manipulate and/or remove tissue. Image (a) represents a surgeon positioned adjacent an operating table on which a patient lies. The control system 18 enables the surgeon to operate the instrument 11 using manual controls that provide control of the cannula 12, the tools 14, and the working elements 28. The system 10 may have means for selectively locking the position of an individual working element 28, for example, so that the surgeon can efficiently operate the working element 28 of a different tool 14. The monitor 20 is located on an opposite side of the operating table to provide the surgeon with a clear view of video images captured within the incision. During the procedure, the distal end 13 of the cannula 12 may be inserted into the patient through an incision 15 to interact with herniated disk material 17.

Figure 3:
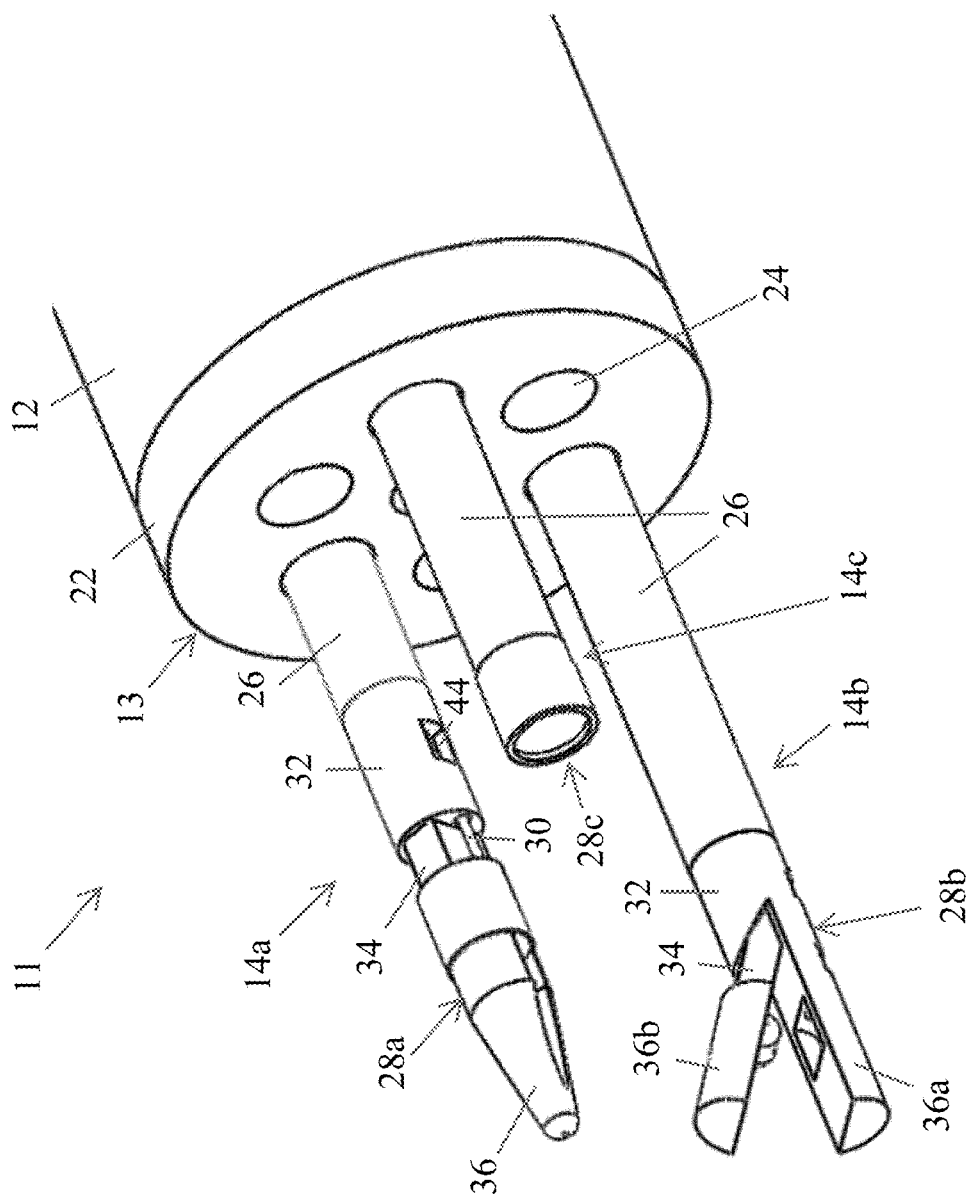
FIG. 3 is an enlarged view of a distal end of the surgical instrument of FIG. 2.

Image (d) of FIG. 2 and FIG. 3 schematically represent the distal end 13 of the cannula 12 as including an adapter 22 comprising several ports 24 from which the tools 14 may protrude. As represented in FIG. 1, the oppositely-disposed proximal end of the cannula 12 also preferably includes a similar adapter 22. Each adapter 22 has multiple ports 24 formed therein that provide spacing between and support for the various tools 14, which preferably are capable of being retracted within the cannula 12. Although represented as through-holes having circular cross-sections, the ports 24 may each individually be any shape and/or size to allow passage through and support of a corresponding tool 14. As a nonlimiting example, one or more of the ports 24 may be through-holes having a circular cross-section having a diameter of 0.125 inch (about 3 mm) or more.

FIG. 8 represents an individual tool 14 as including an elongated shaft 26 having a working element 28 on a distal end thereof. The shaft 26 may be of any diameter (or width) and length, comparable devices being in the nonlimiting ranges of 0.125 inch (about 3 mm) diameter or less and between about 150 and 200 micrometers long. Preferably, the shaft 26 is capable of individually rotating within the cannula 12, and the working elements 28 are capable of articulation relative to the shaft 26. Such functionality provides the ability to change the orientation of the working elements 28 during a surgical procedure without moving the cannula 12, thus reducing damage to tissues surrounding the cannula 12.

As a nonlimiting example, FIG. 3 represents three tools 14a, 14b, and 14c protruding from the distal end 13 of the cannula 12. The tools 14a, 14b, and 14c include working elements 28a, 28b, and 28c on their distal end which are configured to function as a nerve retractor, a grasper, and a camera, respectively. The working element 28a of the tool 14a includes a tip 36 coupled to a base 32 by a flexible joint 34. The base 32 secures the working element 28a to the shaft 26 and may comprise any fastener, threads, or other means for securing the working element 28a to the shaft 26 or may comprise a structure that in conjunction with a fastener is capable of securing the working element 28a to the shaft 26. For example, FIG. 5 represents the working element 28 as comprising a structure 72 for mating with and press-fitting within the shaft 26.

Figure 4:
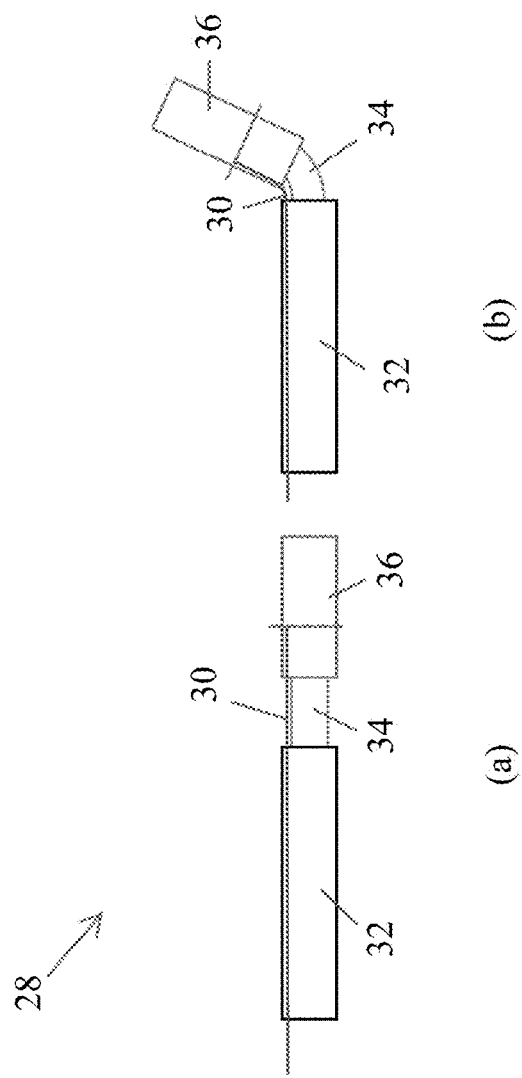
FIG. 4 includes images a and b, which schematically represent articulation of a working element of a tool in accordance with a nonlimiting embodiment of this invention.

FIG. 4 represents a working element 28 of any tool 14, and the manner in which the flexible joint 34 thereof allows the tip 36 to be articulated relative to the base 32. To facilitate such articulation, at least two guide wires 30 may be coupled to the tip 36 and threaded through the working element 28, into the shaft 26, and through the shaft 26 to the proximal end of the cannula 12, where the guide wires 30 may be functionally coupled to, for example, the actuator unit 16 (FIGS. 1, 2, and 8). FIG. 8 represents a nonlimiting embodiment of the actuator unit 16 as connected to the shaft 26 of the tool 14. As also represented in FIG. 8, the actuator unit 16 may comprise servo motors 54 and pulleys 58 for selectively providing or releasing tension on the guide wires 30 to manipulate the working elements 28, an additional servo motor 56 for rotating the shaft 26, and a platform 50, lead screw 53, and stepper motor 60 for retracting or extending the working element 28 mounted on the shaft 26. It should be understood that these components may be substituted with other means capable of selectively providing or releasing tension on the guide wires 30 to retract or extend each tool 14, articulate its working element 28, rotate the working element 28, or otherwise manipulate the tip 36 of the working element 28. Preferably, each working element 28 has a range of motion of at least 80 degrees of rotation (yaw).

The tip 36 of the working element 28 may be any device capable of assisting in the performance of the surgical procedure. For example, in addition to or as alternatives of the retractor 28a, grasper 28b, and camera 28c described for the working elements 28 of FIG. 3, the tip 36 of the working element 28 may be a surgical manipulator (such as but not limited to a rongeur, an elevator, a hook, a curette, a dissector, a scalpel, etc.), a suction tip of an irrigation system, a drill, or any other device.

Figure 5:
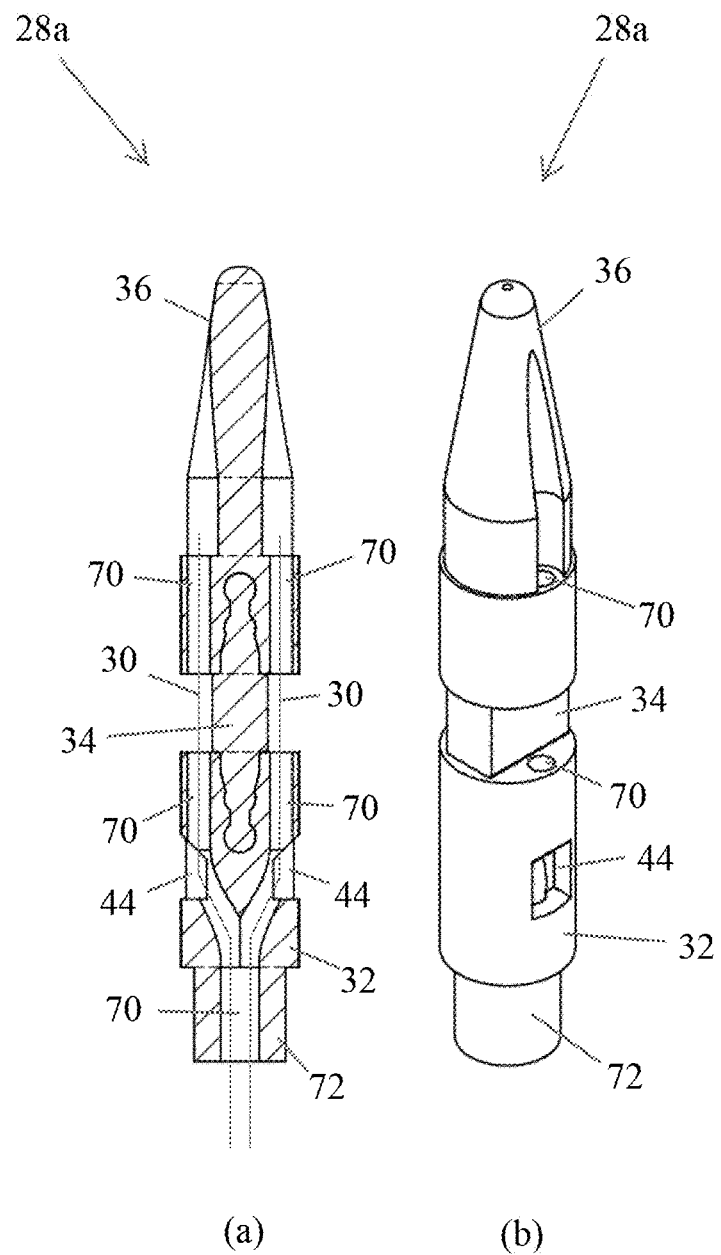
FIG. 5 includes images a and b, which are cross-sectional and perspective views, respectively, that schematically represent a nonlimiting working element configured as a nerve retractor in accordance with a nonlimiting embodiment of this invention.
Figure 6:
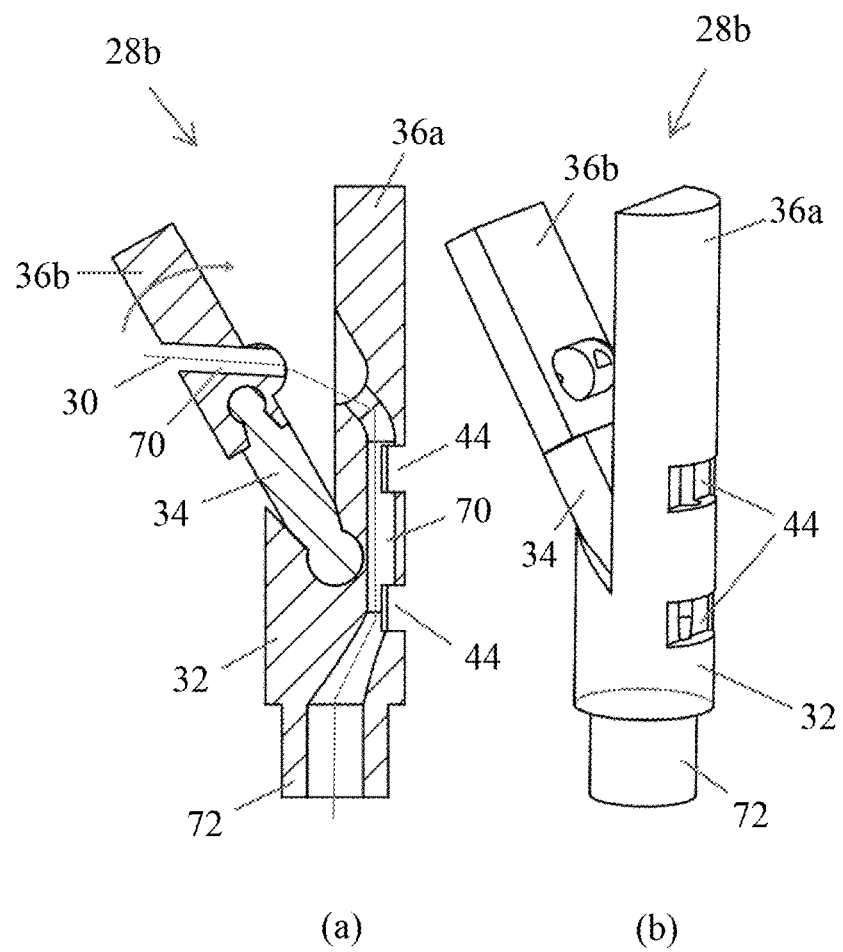
FIG. 6 includes images a and b, which are cross-sectional and perspective views, respectively, that schematically represent a nonlimiting working element configured as a grasper in accordance with a nonlimiting embodiment of this invention.

FIGS. 5 and 6 schematically represent nonlimiting embodiments of the nerve retractor 28a and grasper 28b, respectively, shown in FIG. 3. Images (a) of FIGS. 5 and 6 are cross sectional views of the retractor 28a and grasper 28b, respectively, and images (b) of FIGS. 5 and 6 are perspective views of the retractor 28a and grasper 28b, respectively. As described above in reference to FIG. 4, the retractor 28a if FIG. 5 includes a tip 36 coupled to a base 32 via a flexible joint 34. As represented, the retractor 28a includes passages 70 through which the guide wires 30 may be routed.

Figure 7A:
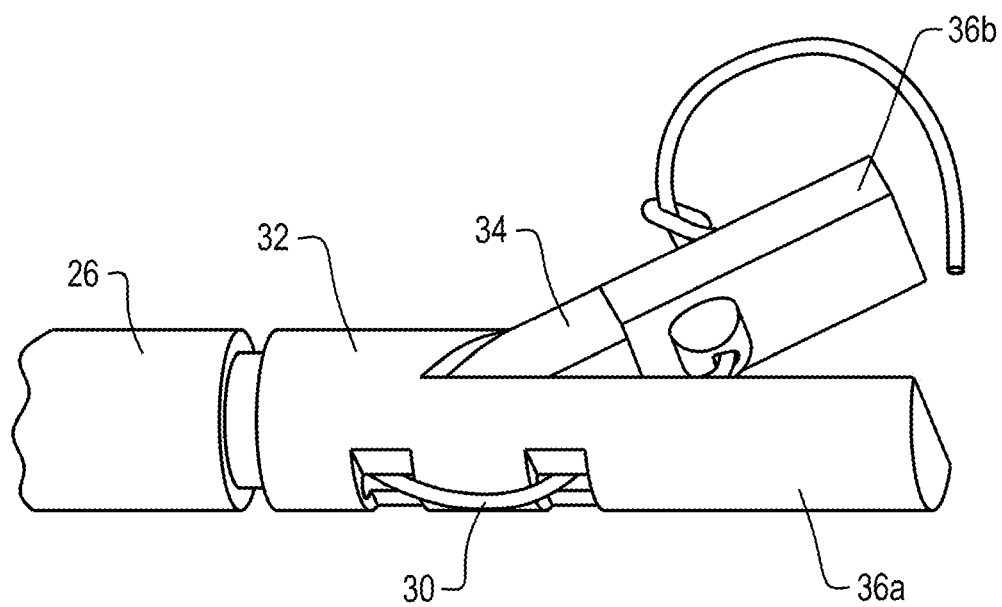
FIGS. 7a and 7b are images that show a grasper type tool in open and closed positions, respectively.
Figure 7B:
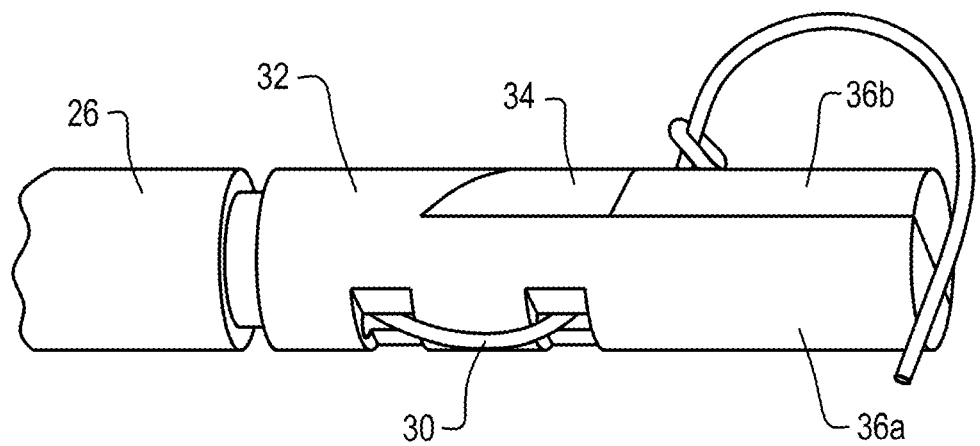
Figure 9B:
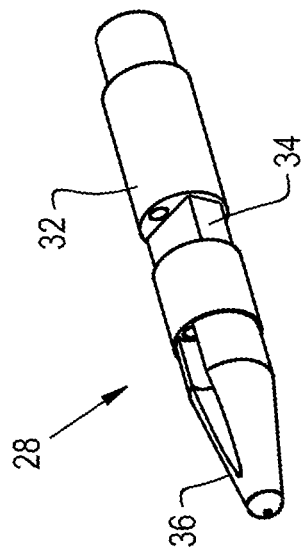
FIGS. 9a, 9b, 9c, and 9d, contain four images that depict the results of steps performed in the production of a working element that was produced with a three-dimensional printing process.
Figure 9D:
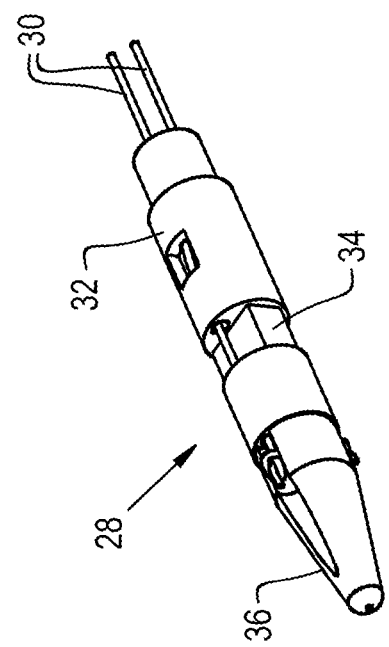
Figure 9A:
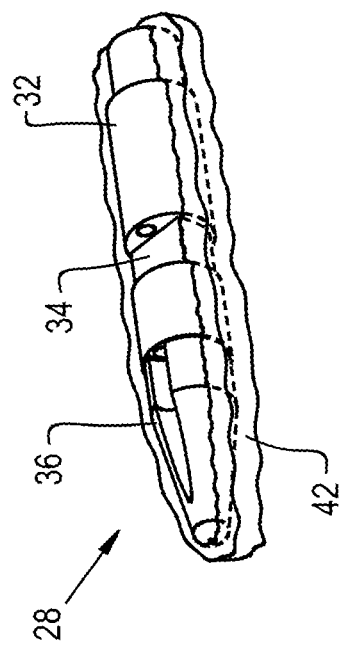
Figure 9C:
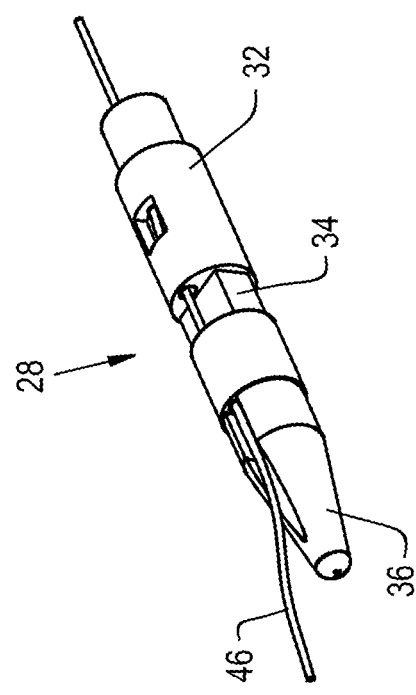

Referring to FIG. 6, the grasper 28b includes a first tip 36a directly coupled to a base 32 and fixed in a permanent position relative thereto, and a second tip 36b coupled to the base 32 by a flexible joint 34. The grasper 28b also includes passages 70 through which a guide wire 30 may be routed. Manipulation of the guide wire 30 provides for articulation of the second tip 36b relative to the base 32 and the first tip 36a. As such, the grasper 28b is capable of providing a gripping functionality by clasping an object between the first and second tips 36a and 36b. FIGS. 7a and 7b represents the grasper 28b in open and closed positions. During the procedure, the nerve retractor 28a of FIG. 5 may be used to articulate and retract a nerve such that the grasper 28b can access the cavity and remove herniated disk material 17 (FIG. 2c).

The various components of working elements 28 (including but not limited to the retractor 28a and grasper 28b) may be formed of a variety of suitable materials. Preferably, the base 32 and the tip 36 are formed of materials sufficiently rigid to perform their intended functions, and the joint 34 is sufficiently pliable or flexible such that the working element 28 may be articulated. Nonlimiting examples include various polymeric and elastic materials. A specific nonlimiting combination of materials includes a rubber-like polymeric material commercially available under the brand name Tango Black™ for the joint 34 and a rigid polymeric material commercially available under the brand name Vero White™ for the base 32 and tip 36, both materials produced by Stratasys Ltd. Alternatively, the two materials may be combined in various ratios individually specific to the base 32, joint 34, and tip 36 which provide a desired stiffness. Preferably, the working elements 28 are relatively small such that they can perform their respective tasks, rotate, and articulate with a confined working space or cavity, including relatively small confined working spaces having a volume of about three centimeters or less.

Although the various components of the working elements 28 could be separately produced and assembled, a preferred but nonlimiting aspect of the invention includes producing one or more of the working elements 28 with an additive manufacturing technique, such as but not limited to a three-dimensional printing technique that forms the various components as a single integral component by fusing particles together with, for example, a scanning electron, laser, or ion beam. Since the various components have different functions, it is likely that they may be formed of different materials, combinations of materials, or different ratios of their respective materials. Therefore, the working elements 28 are preferably produced with a multi-material three-dimensional printer. Forming the working elements 28 with such printing techniques may reduce assembly operations during production, reduce the cost of manufacturing, and/or provide individual users of the system 10 with the capability to design and produce custom working elements 28 to suit their individual needs. It is foreseeable that the working elements 28, especially those produced with an additive manufacturing technique, may have a sufficiently low cost such that they may be considered disposable. Therefore, it is within the scope of the invention that the working elements 28 may be removed from the shaft 26 and disposed after performing the procedure, rather than cleaning or sterilizing them for reuse.

FIG. 9 includes four images (a, b, c, and d) that sequentially represent steps in production of a working element 28 that was formed using an additive manufacturing technique, specifically a three-dimensional printing technique. The working element 28 was printed using a multi-material printer commercially available from Stratasys Ltd. under the brand name Objet350 Connex3™. After printing, the working element 28 was connected to support materials which were used to support and stabilize the working element 28 during the printing process. Image (a) shows the working element 28 encased in an external support material 42, image (b) shows the working element 28 after the external support material 42 has been removed, and image (c) shows a metal wire 46 being used to clear internal support material from passages configured to be used with the guide wires 30. The working element 28 includes ports 44 configured to facilitate removal of the internal support material by reducing the likelihood of clogging within the passages. Image (d) shows the final working element 28 with all support material removed and guide wires 30 routed therethrough.

As represented in FIGS. 1, 2 (image a), and 3, the system 10 may include a camera system that includes a tool 14 comprising a camera as the working element 28c. The camera may include a light source, or the system 10 may separately include a tool 14 with a light source as a working element 28. For example, the working element 28 may include a base 32, a flexible joint 34, and a tip 36 as described in reference to FIG. 4, wherein the tip 36 includes an integrated camera and light source. In such an embodiment, the joint 34 preferably allows the camera and light source to be capable of rotation relative to the cannula 12 and articulation relative to the shaft 26. It is also within the scope of the invention that multiple cameras and/or light sources may be used simultaneously with the system 10. Preferably, the camera and light source fit through the ports 24 in the adapter 22 and are capable of retracting into the body of the cannula 12. FIG. 1 and image (a) of FIG. 2 represent the monitor 20 functionally connected to the camera to provide images and/or video captured by the camera from the inside of the confined working space during the procedure. As nonlimiting examples, the camera and monitor 20 may have wireless communication capabilities or may be coupled with electrical wires routed through the shaft 26 of the tool 14.

The system 10 may include an irrigation system capable of cleaning a lens of the camera, for example, of accumulated fog or blood, or the confined working space in general. Such an irrigation system may include a sheath or tube (not shown) capable of fluidically transporting a cleaning solution and configured to be routed through the cannula 12 and protrude from one of the ports 24 at the distal end 13 of the cannula 12. Such an irrigation system may be capable of providing a cleaning solution to the lens of the camera and to the confined working space in general. The cleaning solution may be a fluid, for example, a gas, liquid, or gas or liquid mixture capable of providing the desired cleaning functionality. For surgical procedures performed within a living body, the cleaning solution may be, but is not limited to, a saline solution.

Figure 10:
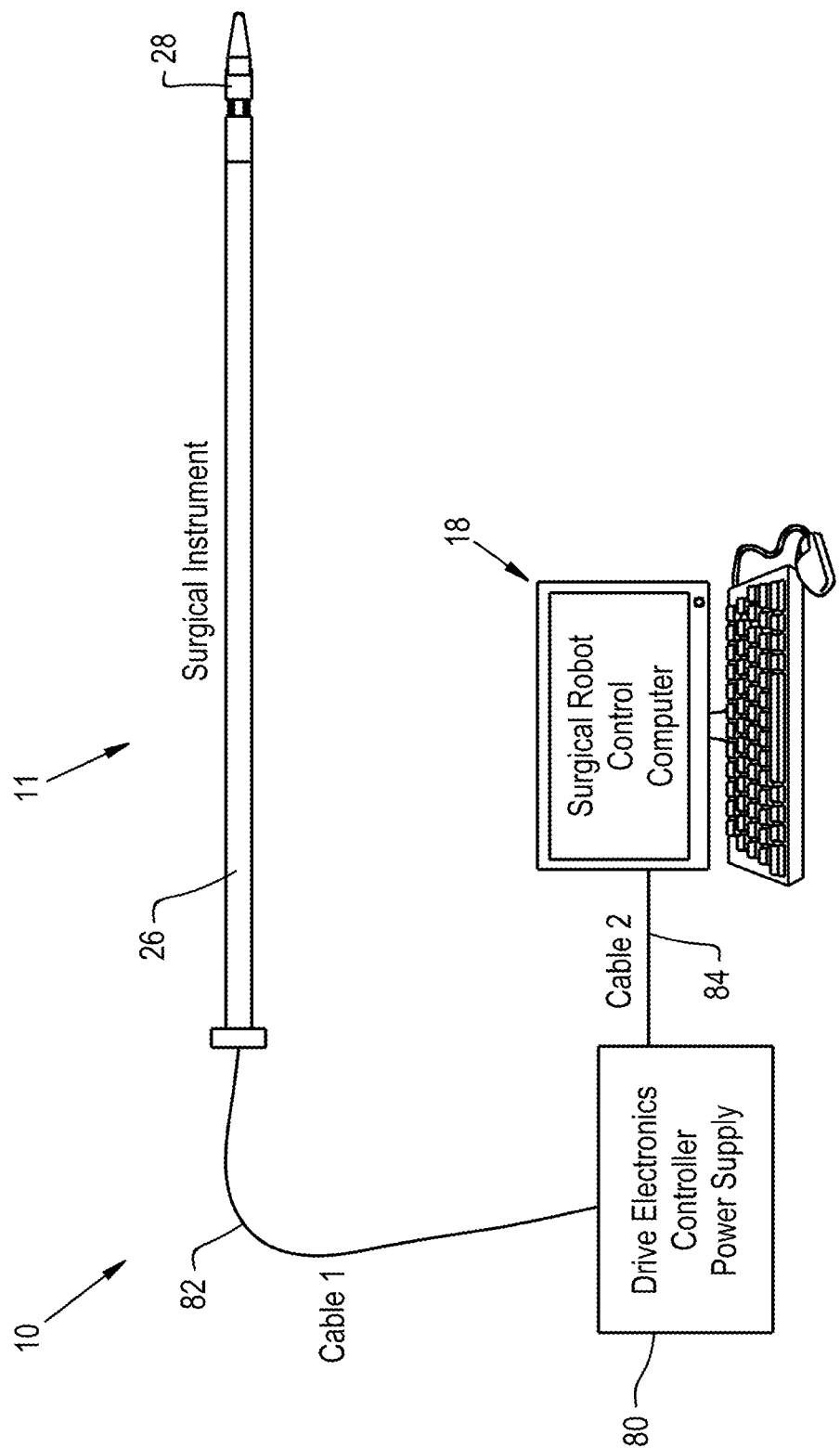
FIGS. 10 and 11 schematically represent alternative systems each comprising a surgical instrument equipped with multiple tools in accordance with a nonlimiting embodiment of this invention.
Figure 11:
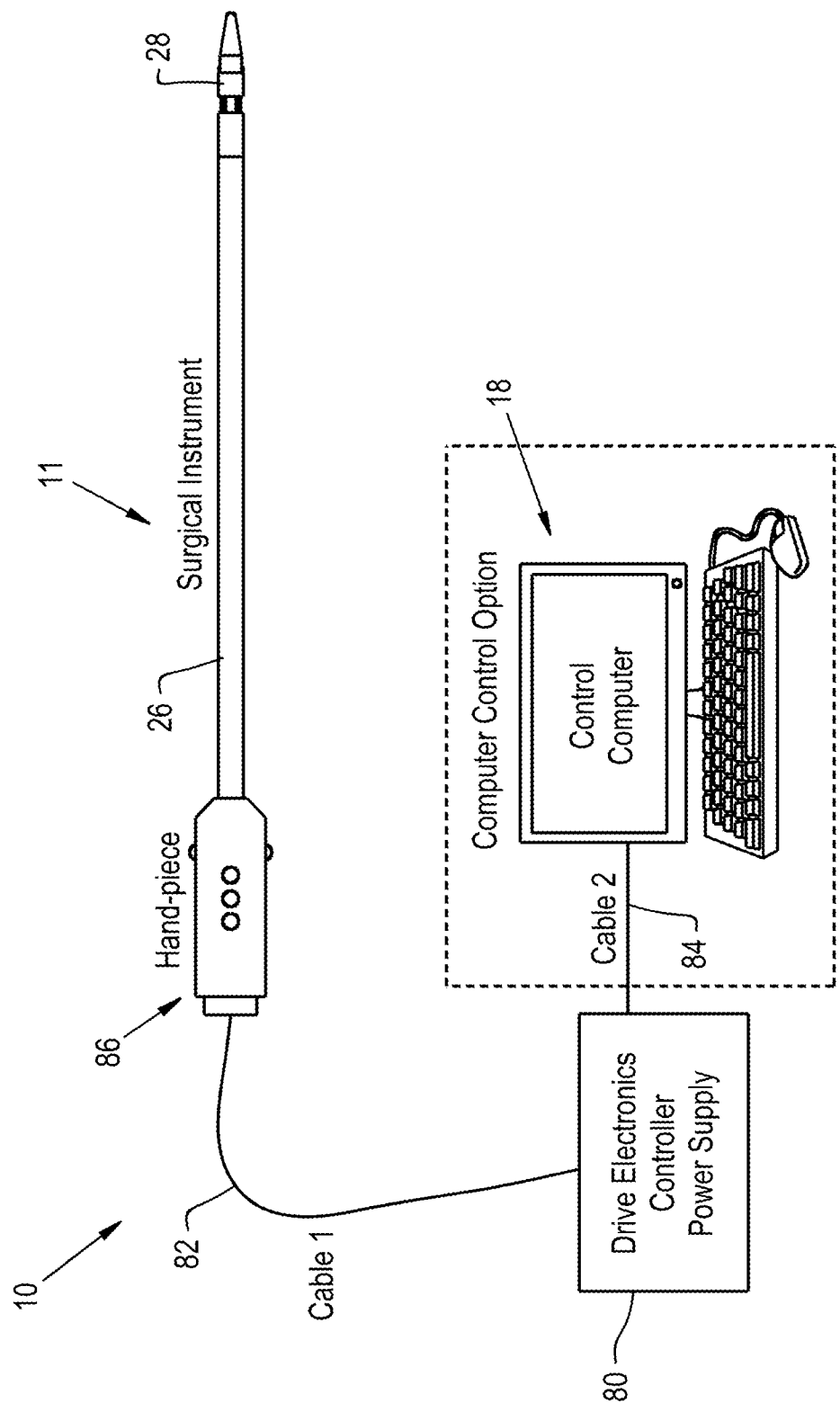

FIGS. 10 and 11 depict two additional embodiments for systems 10 suitable for performing minimally invasive surgery, and in particular the use of minimally invasive robotic spinal surgical instruments 11 that are compatible with, respectively, a surgical robot or an endoscopic system. In FIG. 10, the surgical instrument 11 is connected to a control system 18 in the form of a computer configured and operating as a surgical robot. The instrument 11 is connected to the control system 18 through a control unit 80 via a series of control cables 82 and 84. The control unit 80 comprises a power source, drive electronics, and controller (not shown) capable of translating the computer commands of the control system 18 into signals for actions to be carried out by the instrument 11. In this manner, robotic instrument control is capable of being integrated into the overall control architecture of the system 10.

In FIG. 11, the surgical instrument 11 is similarly connected to a control system 18 through a control unit 80 via a series of control cables 82 and 84. The system 10 primarily differs by the inclusion of an endoscopic hand-piece 86 mounted on the proximal end of the instrument 11, allowing for manual control of the instrument 11 and its working elements 28 instead of the robotic control of FIG. 10. The hand-piece 86 includes interactive controls, as nonlimiting examples, buttons, switches, levers, etc., that allow the operator to control the instrument 11 in the workspace. As such, the cable 84 and control system 18 are not required, but may be included to provide an optional computer mode of operation for the system 10.

In the systems 10 of FIGS. 10 and 11, the instrument 11 and its working elements 28 can be actuated by smart material actuators integrated into the surgical instrument 11 and actuated from the control signals provided by the control system 18 or by the user through the hand-piece 86.

Figure 12:
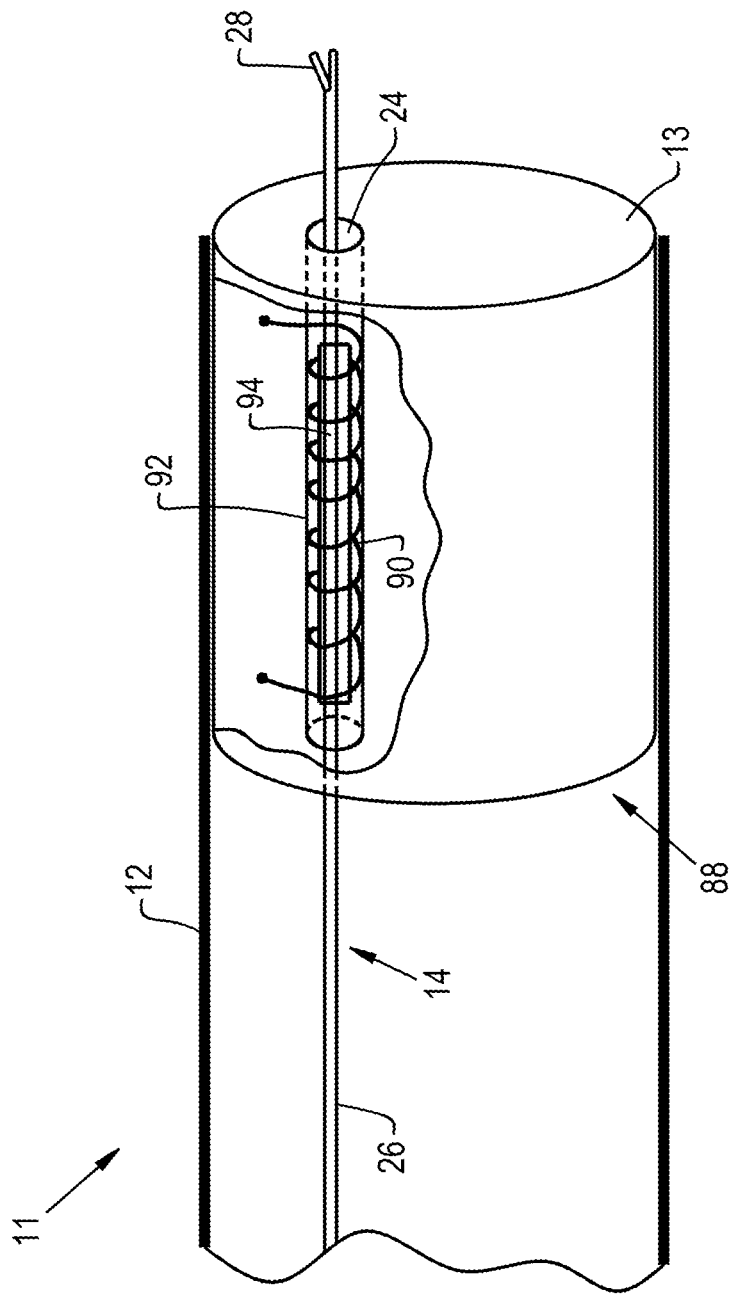
FIG. 12 schematically represents a surgical instrument comprising means for translating a tool thereof in accordance with a nonlimiting embodiment of this invention.
Figure 14:
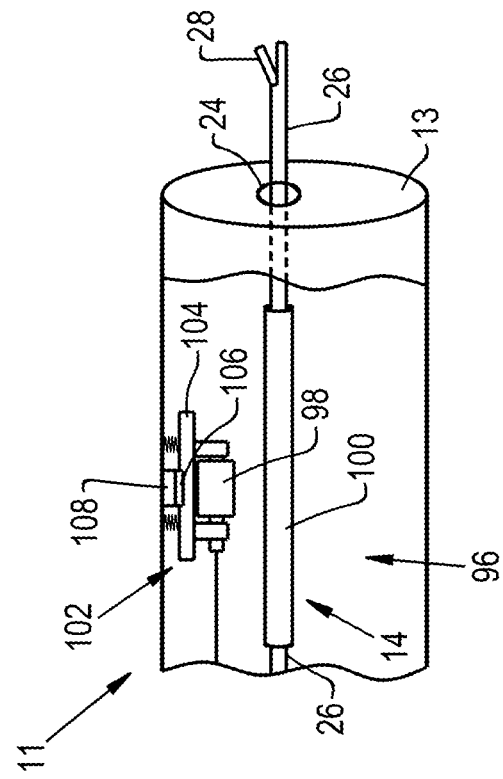
FIGS. 13 and 14 schematically represent a surgical instrument comprising means for rotating a tool thereof in accordance with a nonlimiting embodiment of this invention.
Figure 13:
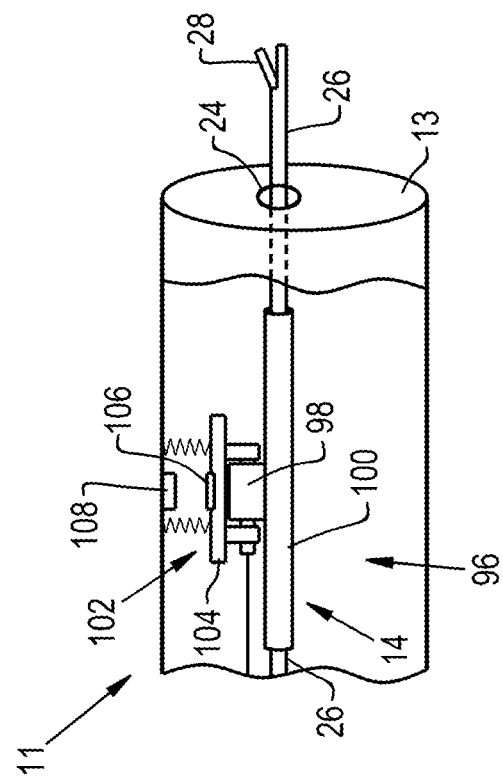

FIGS. 12, 13, and 14 schematically represent the distal end of the cannula 12 of the surgical instrument 11 and indicate how translational and rotational motions of individual tools 14 within the cannula 12 can be achieved with mechanisms internal of the cannula 12. The internal mechanisms are preferably computer controlled to independently translate and/or rotate a tool 14 and its working element 28, shown as protruding from a port 24 of the cannula 12. As such, control schemes previously described can be implemented at least in part with mechanisms integrated into the cannula 12 to allow for the linear translation of tools 14 in and out of a surgical workspace and/or allow for the axial rotation of tools 14 within a surgical workspace.

FIG. 12 represents a mechanism for achieving linear translational control of a tool 14 through the inclusion of a translation unit 88 internal of the cannula 12 and mounted at the distal end 13 of the cannula 12. The translation unit 88 may provide the port 24 through which the tool 14 protrudes from the cannula 12, and in so doing also serves as the adapter 22 described in reference to previous embodiments. The translation unit 88 further includes an actuation coil 90 surrounding a passage 92 within the unit 88 through which the shaft 26 of the tool 14 passes. The shaft 26 of the tool 14 can be formed of metallic material or, as represented in FIG. 12, wrapped with a metallic sheath 94 to enable the shaft 26 to serve as an armature. By causing current to flow through the actuation coil 90, the shaft 26 can function as an electromechanical solenoid to linearly translate the tool 14 and its working element 28. In the embodiment represented in FIG. 12, the shaft 26 will translate in one direction in response to current flow through the coil 26. A spring (not shown) can be integrated into the translation unit 88 to provide a restoring force to move the tool 14 in the opposite direction once current flow is discontinued. Alternatively, a duel solenoid system can be integrated into the translation unit 88 to provide bidirectional linear control of the translation of the tool 14.

FIGS. 13 and 14 represent a mechanism for achieving rotational control of a tool 14 through the inclusion of a rotation unit 96 internal and at the distal end 13 of the cannula 12. Similar to FIG. 12, the rotation unit 96 is depicted as providing the port 24 through which the tool 14 protrudes from the cannula 12. The rotation unit 96 is adapted to cause bidirectional rotational motion about the major axis of the tool 14 with a motorized rotary roller 98 that is in frictional contact with the tool shaft 26. A friction sheath 100 may be attached to the shaft 26 to promote frictional contact with the roller 98. To enable the translational unit 88 of FIG. 12 to be combined with the rotational control of FIGS. 13 and 14, FIGS. 13 and 14 represent an actuator 102 by which the roller 98 can be remotely engaged and disengaged from the shaft 26 of the tool 14. This actuator 102 is represented as comprising a spring-loaded mount 104 that is attached to the interior wall of the cannula 12, a magnet 106 carried by the mount 104, and an electromagnet 108 located on the wall of the cannula 12 opposite the magnet 106. Energizing and de-energizing the electromagnet 108 causes the roller 98 to engage or disengage the shaft 26 of the tool 14.

In view of the foregoing, the systems 10 described above provide functionality that may be used in surgical procedures and provide positive aspects of some of the most popular microdiscectomy procedures in aspects such as incision size and manipulation space utilization. Combined with the dexterity of the articulating working elements 28 and the feature of coordinated manipulation, the systems 10 may significantly aid surgeons in performing surgery and promote improved success rates. This may lead to reduced hospital stays, reduced chances of infection, and quicker recovery for their patients.

As a nonlimiting example, the systems 10 may be used, for example, by a surgeon to perform a surgical procedure within a cavity of a living body by inserting the distal end 13 of the body of the cannula 12 into the cavity of the living body, and therein perform various tasks of the surgical procedure with the working elements 28. Such tasks may require or be promoted by articulating the working element 28 relative to the shaft 26 within the cavity, and/or rotating the working element 28 relative to the cannula 12 within the cavity. It is foreseeable that a surgeon may produce one or more of the working elements 28 with an additive manufacturing technique that forms components of the working element 28 as a single integral component by fusing particles together, and then securing the working element 28 to a distal end of the shaft 26 of the tool 14 prior to performing the surgical procedure.

While the invention has been described in terms of specific embodiments, it is apparent that other forms could be adopted by one skilled in the art. For example, the physical configuration of the systems 10 and their various components could differ from that shown, and materials and processes/methods other than those noted could be used. In addition, the invention encompasses additional or alternative embodiments in which one or more features or aspects of a particular embodiment could be eliminated or two or more features or aspects of different disclosed embodiments could be combined. Accordingly, it should be understood that the invention is not necessarily limited to any embodiment described herein or illustrated in the drawings. Therefore, the scope of the invention is to be limited only by the following claims.

The invention claimed is:

1. A system for performing a surgical procedure within a cavity of a living body, the system comprising:
    a cannula having a tubular body and proximal and distal ends, the distal end being sized and configured to be inserted into the cavity;
    at least first and second tools that individually pass through first and second ports located at the proximal end of the cannula, extend through the body of the cannula, and individually protrude from the distal end of the cannula through additional ports located at the distal end of the cannula, each of the first and second tools comprising a shaft and a working element on a distal end of the shaft, at least a portion of the working element of the first tool being capable of articulation relative to the shaft and rotation relative to the cannula, the working element of the first tool being configured to perform tasks in the cavity, the first and second tools being adapted for translation and rotation relative to the cannula independently of each other;
    a control system and actuator that articulate a tip of the working element of the first tool relative to the shaft of the first tool; and
    a translation unit and a rotation unit disposed within the cannula, the translation unit and the rotation unit comprising mechanisms internal of the cannula for achieving independent translational and rotational motions of the first and second tools within the cannula and to independently translate and rotate the first and second tools and the working elements thereof, the rotation unit comprising a roller that is engageable and disengageable from the shaft of the first tool and an actuator that engages and disengages the roller from the shaft of the tool;
    wherein the working element of the first tool is produced with an additive manufacturing technique that forms components of the working element of the first tool as a single integral component by fusing particles together;
    wherein the working element of the first tool comprises a base configured to removably secure the working element of the first tool to the shaft of the first tool, a tip configured to assist in performance of the surgical procedure, and a joint connecting the base to the tip, the joint being sufficiently flexible such that the tip is capable of articulating relative to the base; and
    wherein the joint is formed of a flexible material such that the tip is able to articulate relative to the base, and the base and the tip are formed of materials that are different than the flexible material of the joint so that the base and the tip are more rigid than the flexible material of the joint.

2. The system of claim 1, wherein the control system comprises a surgical robot that controls the articulation of the working element of the first tool.

3. The system of claim 1, wherein the control system comprises an endoscopic hand-piece for controlling the articulation of the working element of the first tool.

4. The system of claim 1, further comprising computer-controlled means comprising the translation unit for translating the first and second tools relative to the cannula.

5. The system of claim 4, wherein the translation unit is disposed within the cannula at the distal end thereof.

6. The system of claim 5, wherein the translation unit is disposed at one of the additional ports located at the distal end of the cannula.

7. The system of claim 1, further comprising computer-controlled means comprising the rotation unit for rotating the first tool relative to the cannula.

8. The system of claim 7, wherein the rotation unit is disposed within the cannula at the distal end thereof.

9. The system of claim 8, wherein the rotation unit is disposed at one of the additional ports located at the distal end of the cannula.

10. The system of claim 1, further comprising computer-controlled means comprising the translation and rotation units for translating and rotating the first tool relative to the cannula.

11. The system of claim 10, wherein the translation unit and the rotation unit are disposed within the cannula at the distal end thereof.

12. The system of claim 11, wherein at least one of the translation and rotation units is disposed at one of the additional ports located at the distal end of the cannula.

13. The system of claim 11, wherein the working element of the first tool is chosen from the group consisting of graspers and nerve retractors.

14. A system for performing a surgical procedure within a cavity of a living body, the system comprising:
    a cannula having a tubular body and proximal and distal ends, the distal end being sized and configured to be inserted into the cavity;
    at least first and second tools that individually pass through ports located at the proximal end of the cannula, extend through the body of the cannula, and individually protrude from the distal end of the cannula through additional ports located at the distal end of the cannula, each of the first and second tools comprising a shaft and a working element on a distal end of the shaft, at least a portion of the working element of the first tool being capable of articulation relative to the shaft, the working element of the first tool being configured to perform surgical tasks in the cavity, the first and second tools being adapted for translation and rotation relative to the cannula independently of each other;
    a control system and actuator that articulate a tip of the working element of the first tool relative to the shaft of the first tool; and
    computer-controlled means for translating and rotating the first tool relative to the cannula, the computer-controlled means comprising a translation unit and a rotation unit disposed within the cannula at the distal end thereof, the translation unit and the rotation unit comprising mechanisms internal of the cannula for achieving independent translational and rotational motions of the first and second tools within the cannula and to independently translate and rotate the first and second tools and the working elements thereof, the rotation unit comprising a roller that is engageable and disengageable from the shaft of the first tool and an actuator that engages and disengages the roller from the shaft of the tool;

wherein the working element of the first tool is produced with an additive manufacturing technique that forms components of the working element of the first tool as a single integral component by fusing particles together;

wherein the working element of the first tool comprises a base configured to removably secure the working element of the first tool to the shaft of the first tool, a tip configured to assist in performance of the surgical procedure, and a joint connecting the base to the tip, the joint being sufficiently flexible such that the tip is capable of articulating relative to the base; and wherein the joint is formed of a flexible material such that the tip is able to articulate relative to the base, and the base and the tip are formed of materials that are different than the flexible material of the joint so that the base and the tip are more rigid than the flexible material of the joint.

15. The system of claim 14, wherein the control system comprises a surgical robot that controls the articulation of the working element of the first tool.

16. The system of claim 14, wherein the control system comprises an endoscopic hand-piece for controlling the articulation of the working element of the first tool.

17. The system of claim 14, wherein the working element of the first tool is chosen from the group consisting of graspers, nerve retractors, and cameras.

* * * * *